US010357224B2

(12) United States Patent
Robert et al.

(10) Patent No.: US 10,357,224 B2
(45) Date of Patent: Jul. 23, 2019

(54) BEAMFORMING TECHNIQUES FOR ULTRASOUND MICROCALCIFICATION DETECTION

(71) Applicant: KONINKLIJKE PHILIPS N.V., Eindhoven (NL)

(72) Inventors: Jean-Luc Robert, White Plains, NY (US); Sheng-Wen Huang, Ossining, NY (US); Emil George Radulescu, Ossining, NY (US); Francois Guy Gerard Marie Vignon, Croton-on-Hudson, NY (US); Ramon Quido Erkamp, Yorktown Heights, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 975 days.

(21) Appl. No.: 14/777,564

(22) PCT Filed: Mar. 12, 2014

(86) PCT No.: PCT/IB2014/059657
§ 371 (c)(1),
(2) Date: Sep. 16, 2015

(87) PCT Pub. No.: WO2014/147517
PCT Pub. Date: Sep. 25, 2014

(65) Prior Publication Data
US 2016/0296202 A1 Oct. 13, 2016

Related U.S. Application Data

(60) Provisional application No. 61/803,634, filed on Mar. 20, 2013, provisional application No. 61/907,022, filed on Nov. 21, 2013.

(51) Int. Cl.
*A61B 8/00* (2006.01)
*A61B 8/08* (2006.01)

(52) U.S. Cl.
CPC ............ *A61B 8/085* (2013.01); *A61B 8/0825* (2013.01); *A61B 8/461* (2013.01); *A61B 8/5207* (2013.01); *A61B 8/5223* (2013.01)

(58) Field of Classification Search
CPC .................................................... A61B 8/085
See application file for complete search history.

(56) References Cited

U.S. PATENT DOCUMENTS 5,999,639 A * 12/1999 Rogers ...................... B25J 15/04
382/132
6,071,240 A * 6/2000 Hall ..................... G01S 7/52026
600/443

(Continued)

FOREIGN PATENT DOCUMENTS

CN 101378700 A 3/2009
WO 2006009469 A2 1/2006

OTHER PUBLICATIONS

Yu et al "Generalized Eigenspace-Based Beamformers" IEEE Transactions on Signal Processing, vol. 43, No. 11, Nov. 1995 p. 2453-2461.

(Continued)

*Primary Examiner* — Jason Skaarup (57) ABSTRACT

A medical ultrasound acquisition-data analysis device acquires channel data (144) via ultrasound received on the channels, uses the acquired channel data to estimate data coherence and derive dominance of an eigen-value of a channel covariance matrix and, based on the estimate and dominance, distinguishes microcalcifications (142) from background. Microcalcifications may then be made distinguishable visually on screen via highlighting, coloring, annotation, etc. The channel data operable upon by the (Continued)

estimating may have been subject to beamforming delays and may be summed in a beamforming procedure executed in the estimating. In the estimating and deriving, both field point-by-field point, multiple serial transmits (116, 118) may be used for each field point. In one embodiment results of the estimating and deriving are multiplied point-by-point and submitted to thresholding.

24 Claims, 6 Drawing Sheets

(56) References Cited

U.S. PATENT DOCUMENTS

| | | | | |
|---|---|---|---|---|
| 6,117,080 | A | 9/2000 | Schwartz | |
| 6,827,685 | B2* | 12/2004 | Lin | G01S 7/52046 600/437 |
| 7,921,717 | B2* | 4/2011 | Jackson | G03B 42/06 600/443 |
| 8,184,927 | B2* | 5/2012 | Lankoande | G01S 13/9035 382/260 |
| 8,216,141 | B2* | 7/2012 | Ahn | G01S 7/52025 600/437 |
| 8,317,712 | B2 | 11/2012 | Burcher | |
| 9,271,697 | B2* | 3/2016 | Teo | A61B 8/14 |
| 9,275,630 | B2* | 3/2016 | Blalock | G01S 7/52085 |
| 9,482,736 | B1* | 11/2016 | Ray | G01S 3/808 |
| 9,945,946 | B2* | 4/2018 | Dokmanic | G01S 15/89 |
| 2005/0228279 | A1* | 10/2005 | Ustuner | G01S 7/52049 600/443 |
| 2006/0171573 | A1 | 8/2006 | Rogers | |
| 2009/0247869 | A1 | 10/2009 | Rambod | |
| 2010/0266179 | A1* | 10/2010 | Ramsay | G06T 7/0012 382/131 |
| 2015/0342567 | A1* | 12/2015 | Ustuner | G10K 11/346 600/447 |
| 2016/0084948 | A1* | 3/2016 | Dahl | A61B 8/4483 367/7 |

OTHER PUBLICATIONS

Asl et al "Eigenspace-Based Minimum Variance Beamforming Applied to Medical Ultrasound Imaging" IEEE Transactions on Ultrasonics, Ferroelectrics, and Frequency Control. vol. 57, No. 11, Nov. 2010 p. 2381-2390.

Asl et al "Minimum Variance Beamforming Combined With Adaptive Coherence Weighting Applied to Medical Ultrasound Imaging" IEEE Transactions on Ultrasonics, Ferroelectrics and Frequency Control. vol. 56, No. 9, Sep. 2009 p. 1923-1931.

Huang, Sheng-Wen et al "Ultrasonic Computed Tomography Reconstruction of the Attunuation Coefficient Using a Linear Array" IEEE Transactions on Ultrasonics, Ferroelectrics, and Frequency Control, vol. 52, No. 11, Nov. 2005, pp. 2011-2022.

Christoyianni, I. et al "Computer Aided Diagnosis of Breast Cancer in Digitized Mammograms", Computerized Medical Imaging and Graphics, vol. 26, No. 5, 2002, pp. 309-319.

Jensen, Jorgen Arendt et al "Synthetic Aperture Ultrasound Imaging", Sciencedirect, Ultrasonics, vol. 44, 2006, pp. e5-e15.

Robert, Jean-Luc et al "Green's Function Extimation in Speckle using the Decomposition of the Time Reversal Operator: Application to Aberration Correction in Medical Imaging", Journal Acoustical Society of America, vol. 123, Feb, 2008, pp. 866-877.

Montaldo, Gabriel et al "Coherent Plane-Wave Compounding for Very High Frame Rate Ultrasonography and Transient Elastography", IEEE Transactions on Ultrasonics, Ferroelectrics, and Frequency Control, vol. 56, No. 3, Mar. 2009, pp. 489-506.

Mallart, Raoul et al "Adaptive Focusing in Scattering Media Through Sound-Speed Inhomogeneities: The Van Cittert Zernike Approach and Focusing Criterion", Journal Acoustical Society of America, vol. 96, No. 6, Dec. 1994, pp. 3721-3732.

\* cited by examiner

FIG. 1

$$CF(m,rx) \equiv \frac{\sum_{tx=rx-\Delta}^{rx+\Delta} \left| \sum_{n=1}^{N} S(m,n,tx,rx) \right|^2}{\sum_{tx=rx-\Delta}^{rx+\Delta} N \sum_{n=1}^{N} \left| S(m,n,tx,rx) \right|^2} \quad \text{(definition 1)}$$

204 → $CF$; 208 → numerator; 206 → denominator $$R(m,rx) \equiv \frac{1}{2d+1} \sum_{p=m-d}^{m+d} s(p,rx) s^H(p,rx) \quad \text{(definition 2)}$$

210, 230, 214, 222, 220

$$\text{where} \quad s(p,rx) = \begin{bmatrix} S(p,1,rx,rx) \\ S(p,2,rx,rx) \\ \vdots \\ S(p,N,rx,rx) \end{bmatrix} \quad \text{(definition 3)}$$

$$\text{Tr}\{R(m,rx)\} \equiv \sum_{i=1}^{N} R_{ii}(m,rx) = \sum_{i=1}^{N} \gamma_i(m,rx) \quad \text{(definition 4)}$$

212

$$ev_d(m,rx) \equiv \frac{1}{1 - \dfrac{\gamma_1(m,rx)}{\text{Tr}\{R(m,rx)\}}} \quad \text{(definition 5)}$$

216, 218, 228

$$R(m,rx) \equiv \frac{1}{(2d+1)(2g+1)} \sum_{p=m-d}^{m+d} \sum_{tx=rx=g}^{rx+g} s(p,tx,rx) s^H(p,tx,rx) \quad \text{(definition 6)}$$

226, 224

$$\text{where} \quad s(p,tx,rx) = \begin{bmatrix} S(p,1,tx,rx) \\ S(p,2,tx,rx) \\ \vdots \\ S(p,N,tx,rx) \end{bmatrix} \quad \text{(definition 7)}$$

BEAMFORMING TECHNIQUES FOR ULTRASOUND MICROCALCIFICATION DETECTION

CROSS-REFERENCE TO PRIOR APPLICATION

This application is the U.S. National Phase Application under 35 U.S.C. § 371 of International Application No. PCT/IB2014/059657, filed on Mar. 12 2014, which claims the benefit of U.S. Provisional Patent Application No. 61/803,634, filed Mar. 20, 2013 and U.S. Provisional Patent Application No. 61/907,022, filed Nov. 21, 2013. These applications are hereby incorporated by reference herein.

FIELD OF THE INVENTION

The present invention relates to medical imaging for identifying microcalcifications and, more particularly, to use of ultrasound as the imaging modality.

BACKGROUND OF THE INVENTION

Mammography's success for screening for breast cancer is mostly attributed to its capability for reliably imaging calcifications, an important marker for early stage breast cancer. Microcalcifications are present in 60-80% of breast cancers and are a reliable indicator of both benign and malignant lesions. The key diagnostic features of microcalcifications are their location, number, size, morphology, distribution, pattern, and relation to a mass. These features help stratify the risk of malignancy and often are the only marker of cancer. A relevant example is Ductal Carcinoma in Situ (DCIS), which accounts for 20% of breast cancers.

However, mammography shows poor performance in dense breast tissue, the non-fatty portion of the breast. Dense breast tissue is more commonly found in younger women, and women in certain localities, China for example.

Also, despite measures to reduce the dose, mammography exposes the patient to ionizing radiation. In addition, there is the issue of patient comfort due to the need for compression plates.

The major limitation of conventional ultrasound, which is non-ionizing and needs no compression plates, is its poor sensitivity to microcalcifications. The sensitivity to microcalcifications is within 50-80%.

Mallart discloses phase aberration correction of an ultrasonic transmit beam for the inhomogeneities of a medium through the use of a receive focusing criterion that is independent of both the scattering cross-section of the medium and the transmitted energy. See R. Mallart and M. Fink, "Adaptive focusing in scattering media through sound-speed inhomogeneities: The van Cittert Zernike approach and focusing criterion," J. Acoust. Soc. Am., vol. 96, no. 6, pp. 3721-3732, 1994.

SUMMARY OF THE INVENTION

What is proposed herein below is directed to addressing one or more of the above concerns.

Channel data contain much more information than B-mode images obtained after ultrasound receive beamforming. Therefore, channel-data-based beamforming techniques can provide better sensitivity and/or specificity for microcalcification detection than image processing techniques. The novel technology proposed herein enhances the contrast between microcalcifications and the background, i.e., body tissue in which the calcifications reside, typically soft tissue such as dense breast tissue.

In addition to the advantages noted above in using ultrasound for early-stage breast cancer detection, the screening and follow-up diagnostic procedures will be greatly simplified due to medical evaluation using only one modality. Also, good sensitivity to microcalcifications will facilitate easier identification of tumor location in ultrasound-guided biopsies, improving the workflow and diagnostic confidence.

In accordance with what is proposed herein, a medical ultrasound acquisition-data analysis device having channels is configured for: acquiring channel data via ultrasound received on the channels; using the acquired channel data to estimate coherence of the data and to derive dominance of an eigenvalue of a channel covariance matrix; and, based on the estimate and the derived dominance, distinguishing microcalcifications from background.

For such a device, a computer readable medium or alternatively a transitory, propagating signal is part of what is proposed herein. A computer program embodied within a computer readable medium as described below, or, alternatively, embodied within a transistory, propagating signal, has instructions executable by a processor for performing the acts of: using acquired channel data to estimate coherence of the data and to derive dominance of an eigenvalue of a channel covariance matrix; and, based on the estimate and the derived dominance, distinguishing microcalcifications from background.

Details of the novel, ultrasonic microcalcification identification technology are disclosed below with the aid of the following drawing, which is not drawn to scale, and the following formula sheet and flow charts.

DETAILED DESCRIPTION OF EMBODIMENTS

Figure 1:
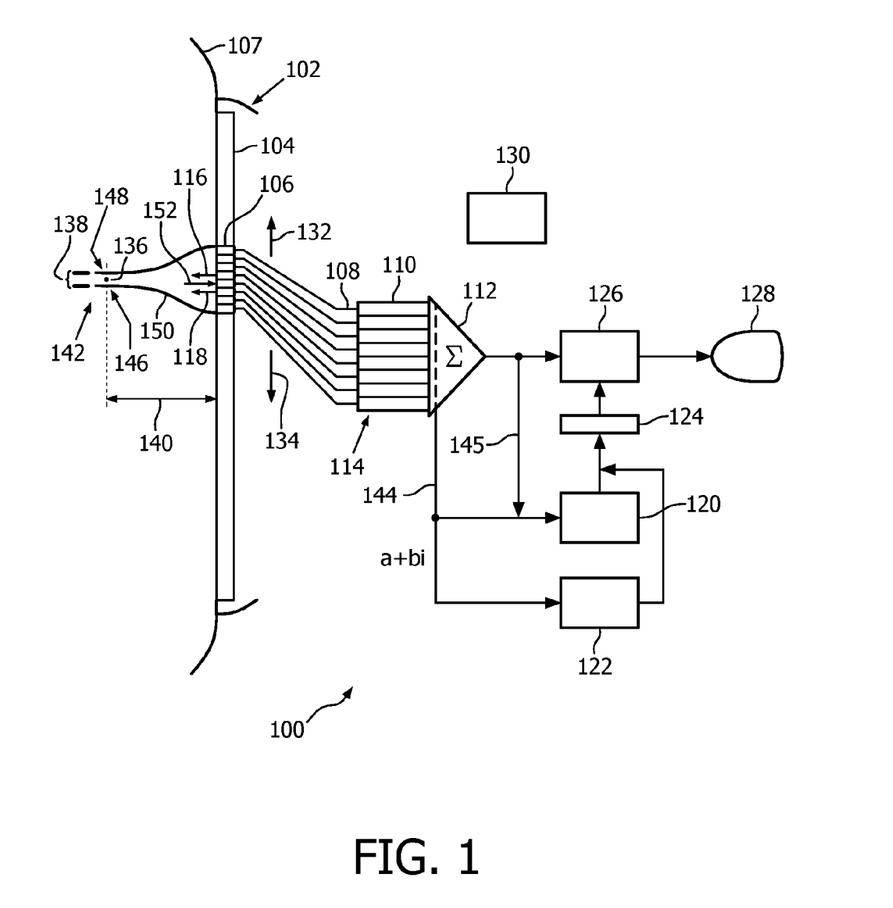
FIG. 1 is a schematic diagram of an ultrasonic microcalcification identification device in accordance with the present invention.

FIG. 1 depicts, by way of illustrative and non-limitative example, a medical ultrasound acquisition-data analysis device characterizable as an ultrasonic microcalcification identification device 100.

The device 100 includes an ultrasound imaging probe 102 having an array 104 of transducer elements 106. The probe 102 is shown as pressed into acoustic contact with breast tissue 107.

The device 100 further includes channels 108 in connection with the elements 106. The channels have respective sample delay elements 110. The latter connect to a coherent summer 112, the summer and the receive delay elements 110 together constituting a receive beamformer 114. The delay elements 110 may be augmented to also provide amplitude weighting. Delay elements for steering and focusing transmit beams 116, 118 can be implemented and are not shown. The multiple transmit beams 116, 118 may be parallel, or may be differently angled, i.e., steered.

Also included in the device 100 are a coherence factor (CF) determination module 120, an eigenvalue dominance determination module 122, a microcalcification identification module 124, a signal and image processor 126, a display 128, and a scanning controller 130. The controller 130 controls the scanning as indicated by the oppositely-oriented scanning directional arrows 132, 134 in FIG. 1, and the other components of the device 100 shown in FIG. 1.

The beamforming strategy for microcalcification detection is to involve channel-data-based parameters that favor point targets 136, smaller than a spatial resolution, such as the lateral resolution 138 at that imaging depth 140. Microcalcifications 142 resemble such targets 136 acoustically.

The microcalcification 142 is the dominant scatterer in its resolution cell and causes isotropic scattering. A coherence factor and an eigenvalue dominance criterion, both discussed herein below, are utilized to respectively assess the isotropic scattering and the dominance of the microcalcification. In the background tissue there is no such dominance of a single, isotropic scatterer.

Two parts of a bifurcated approach proposed herein accordingly are coherence estimation using multiple transmit beams and covariance matrix analysis to extract eigenvalues.

More generally, it is noted at the outset that channel data, after applying beamforming delays but before coherent summing, i.e., "post-delay channel data", 144 is outputted by the summer 112. This is complex data generally in the form "a+bi", as shown in FIG. 1, i.e., such that both the real and imaginary components of a datum can be nonzero. The channel data 144 is routed to the eigenvalue dominance determination module 122. The same data 144 is routable to the CF module 120 for summing there, although summing can alternatively, or in addition, be performed in the summer 112 as seen from the alternative path 145 in FIG. 1. Also, the beamforming done by the CF module 120 can stand alone in forming field points for further image processing in the signal and image processor 126. Or, alternatively or in addition, summed output of the summer 112, which may for example be subject, in the summer, to amplitude weighting, can be submitted for processing by the signal and image processor 126. In either event, the signal and image processor 126 prepares the beamformed data for display, performing functions such as frequency compounding, logarithmic compression and scan conversion.

Referring now to the first part of the bifurcated approach, coherence estimation, let $S(m, n, tx, rx)$ denote complex RF channel data (or "delayed data") 144, i.e., after applying beamforming delays and optionally amplitude weighting. Here, m is the imaging depth/time counter or index, n the channel index, tx the transmit beam index, and rx the receive beam index. A coherence factor (CF) or "focusing criterion" at a spatial point (m, rx), or field point, 146 with a single transmit beam 116 is:

$$CF_0(m, rx) \equiv \frac{\left|\sum_{n=1}^{N} S(m, n, rx, rx)\right|^2}{N \sum_{n=1}^{N} |S(m, n, rx, rx)|^2} = \frac{\left|\frac{1}{N}\sum_{n=1}^{N} S(m, n, rx, rx)\right|^2}{\frac{1}{N}\sum_{n=1}^{N} |S(m, n, rx, rx)|^2},$$

where N is the number of channels 108. The term $$\left|\frac{1}{N}\sum_{n=1}^{N} S(m, n, rx, rx)\right|^2$$

is denoted as $I_c(m, rx)$, where the subscript "c" stands for coherent, as it can be interpreted as the average coherent intensity over channels at the point (m, rx). The denominator on the right can be expressed as $$\frac{1}{N}\sum_{n=1}^{N} |S(m, n, rx, rx)|^2 =$$

$$\frac{1}{N}\sum_{n=1}^{N} |\Delta S(m, n, rx, rx)|^2 + \left|\frac{1}{N}\sum_{n=1}^{N} S(m, n, rx, rx)\right|^2$$

where $$\Delta S(m, n, rx, rx) = S(m, n, rx, rx) - \frac{1}{N}\sum_{n=1}^{N} S(m, n, rx, rx).$$

The term $$\frac{1}{N}\sum_{n=1}^{N} |\Delta S(m, n, rx, rx)|^2$$

is denoted as $I_{inc}(m, rx)$, where the subscript "inc" stands for incoherent. This is because $I_{inc}(m, rx)$ reflects the average intensity of incoherent signals (in the surroundings of (m, rx) decided by the focusing quality on transmit) and is zero when the channel data 144 are fully coherent. Substituting terms, $$CF_0(m, rx) = \frac{I_c(m, rx)}{I_{inc}(m, rx) + I_c(m, rx)} = \frac{1}{\frac{I_{inc}(m, rx)}{I_c(m, rx)} + 1}.$$

Therefore, $CF_0(m, rx)$ indicates how much the point (m, rx) is brighter than its surroundings. $CF_0$ ranges between 0 and 1 and it reaches the maximum 1 if and only if the channel data 144 are fully coherent. Full coherence means that $S(m, 1, rx, rx) = S(m, 2, rx, rx) = \ldots = S(m, N, rx, rx)$. Around a strong point target or a reflector, the $CF_0$ value is high.

Figure 2:
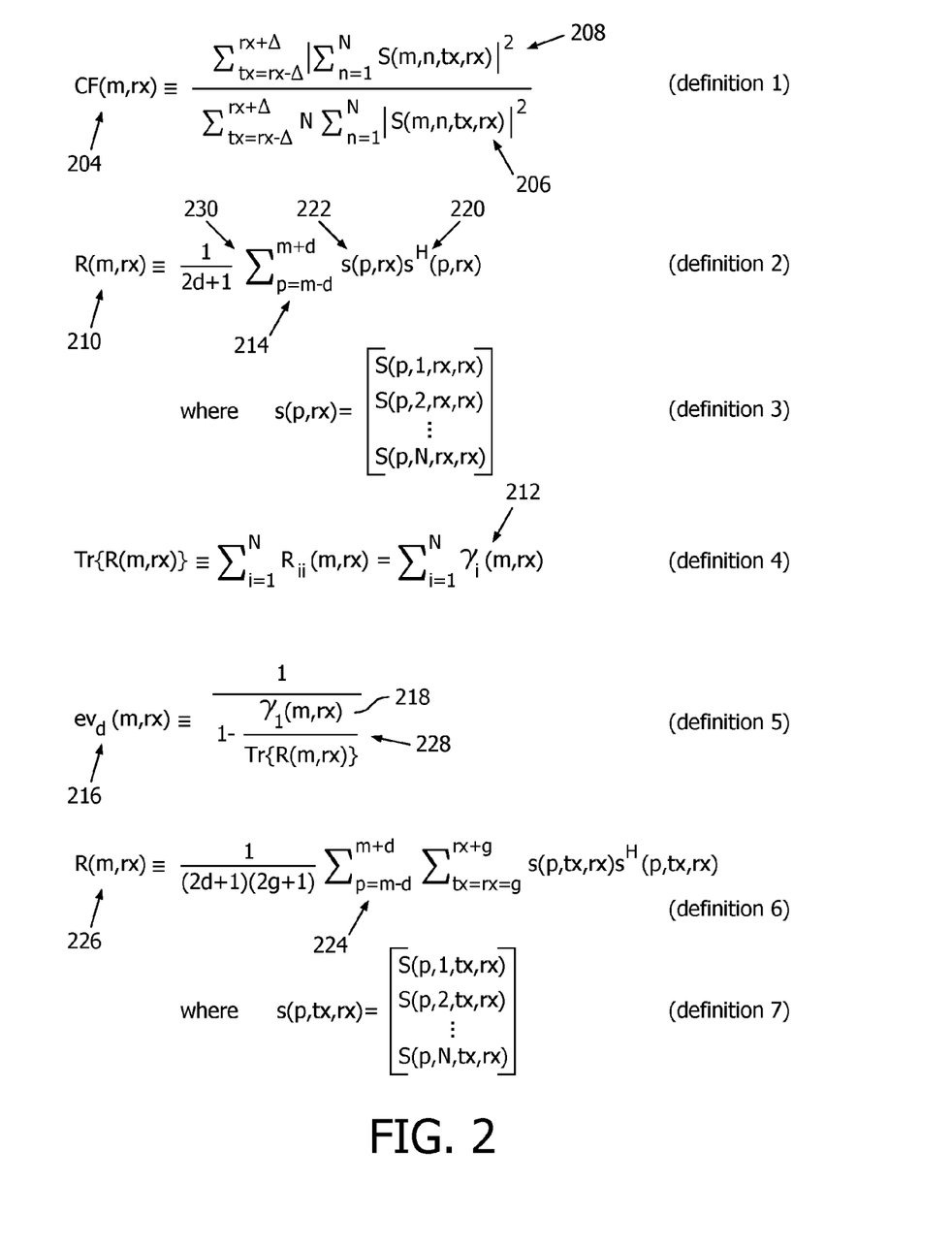
FIG. 2 is a set of exemplary mathematical definitions and relationships in accordance with the present invention.

To distinguish point targets, which microcalcifications 142 in background tissue 148 resemble acoustically, from planar reflectors, multiple transmit beams 116, 118 can be incorporated into CF estimation. CF is thereby redefinable as:

$$CF(m, rx) \equiv \frac{\sum_{tx=rx-\Delta}^{rx+\Delta} \left|\sum_{n=1}^{N} S(m, n, tx, rx)\right|^2}{\sum_{tx=rx-\Delta}^{rx+\Delta} N \sum_{n=1}^{N} |S(m, n, tx, rx)|^2} \quad \text{(definition 1)}$$

which definition, like the ones that follow, is repeated in FIG. 2.

As mentioned above, the spatial point (m, rx) 146 is a function of both an associated receive beam rx 150 and a spatial depth 140 or time. The estimating operates on the delayed data 144 by summing, thereby performing beamforming. The CF(m, rx) estimate, or result of the estimating, 204 includes spatial compounding of the CF by summing, over multiple transmit beams 116, 118, a squared-magnitude function 206 and a squared beamsum 208, i.e. summed result of beamforming. The function 206 and beamsum 208 are both formed by summing over the channels 108.

Referring now to the second part the bifurcated approach, let R(m, rx) denote a covariance matrix, or "correlation/covariance matrix", 210 at the point (m, rx) obtained by temporal averaging over a range 214 of time or spatial depth 140:

$$R(m, rx) \equiv \frac{1}{2d+1} \sum_{p=m-d}^{m+d} s(p, rx)s^H(p, rx) \quad \text{(definition 2)}$$

where $$s(p, rx) = \begin{bmatrix} S(p, 1, rx, rx) \\ S(p, 2, rx, rx) \\ \vdots \\ S(p, N, rx, rx) \end{bmatrix}. \quad \text{(definition 3)}$$

As R(m, rx) is positive semidefinite, all of its eigenvalues 212 are real and nonnegative. Denote the eigenvalues by $\{\gamma_i(m, rx)\}_{i=1}^N$ with $\gamma_i \geq \gamma_{i+1}$. Then the trace of R(m, rx) is $$Tr\{R(m, rx)\} \equiv \sum_{i=1}^N R_{ii}(m, rx) = \sum_{i=1}^N \gamma_i(m, rx). \quad \text{(definition 4)}$$

The dominance 216 of the first eigenvalue 218 is represented as $$ev_d(m, rx) \equiv \frac{1}{1 - \frac{\gamma_1(m, rx)}{Tr\{R(m, rx)\}}}. \quad \text{(definition 5)}$$

It is infinite if $\gamma_i(m, rx)=0$ for $i \geq 2$ (i.e., if the rank of R(m, rx) is 1) as $Tr\{R(m, rx)\}=\gamma_1(m, rx)$, and finite otherwise. Summing over several transmits 116, 118 (beam averaging) could also be applied in correlation matrix analysis, as follows:

$$R(m, rx) \equiv \quad \text{(definition 6)}$$
$$\frac{1}{(2d+1)(2g+1)} \sum_{p=m-d}^{m+d} \sum_{tx=rx-g}^{rx+g} s(p, tx, rx)s^H(p, tx, rx)$$

where $$s(p, tx, rx) = \begin{bmatrix} S(p, 1, tx, rx) \\ S(p, 2, tx, rx) \\ \vdots \\ S(p, N, tx, rx) \end{bmatrix}. \quad \text{(definition 7)}$$

Another way of combining transmits is to form the covariance matrix from data generated by an algorithm that recreates focused transmit beams retrospectively. An example utilizing retrospective dynamic transmit (RDT) focusing is as follows, and, for other such algorithms such as plane wave imaging (see G. Montaldo, M. Tanter, J. Bercoff, N. Benech, and M. Fink, "Coherent plane-wave compounding for very high frame rate ultrasonography and transient elastography," IEEE Trans. Ultrason. Ferroelectr. Freq. Control, vol. 56, no. 3, pp. 489-506, 2009) and synthetic aperture beamforming (see J. A. Jensen, S. I. Nikolov, K. L. Gammelmark, and M. H. Pedersen, "Synthetic aperture ultrasound imaging," Ultrasonics, vol. 44, supplement, pp. e5e15, 2006), analogous eigenvalue dominance computations apply:

$$R(m, rx) \equiv \frac{1}{2d+1} \sum_{p=m-d}^{m+d} s_{RDT}(p, rx)s_{RDT}^H(p, rx)$$

where $$s_{RDT}(p, rx) = \begin{bmatrix} S_{RDT}(p, 1, rx) \\ S_{RDT}(p, 2, rx) \\ \vdots \\ S_{RDT}(p, N, rx) \end{bmatrix},$$

and $S_{RDT}(p, n, rx)$ are the dynamically transmit-beamformed complex RF channel data obtained by performing retrospective dynamic transmit (RDT) focusing on the original channel data S(m, n, tx, rx). See U.S. Pat. No. 8,317,712 to Burcher et al., the entire disclosure of which is incorporated herein by reference.

In the above bifurcated approach, $CF_0(m, rx)$ or $CF(m, rx)$ can, as with the dominance, likewise be obtained by temporal averaging over a range 214 of time or spatial depth 140. Coherence factor can also be estimated using dynamically transmit-beamformed channel data as follows:

$$CF_{RDT}(m, rx) \equiv \frac{\left| \sum_{n=1}^N S_{RDT}(m, n, rx) \right|^2}{N \sum_{n=1}^N |S_{RDT}(m, n, rx)|2}.$$

According to J. R. Robert and M. Fink, "Green's function estimation in speckle using the decomposition of the time reversal operator: Application to aberration correction in medical imaging," J. Acoust. Soc. Am., vol. 123, no. 2, pp. 866-877, 2008, the dominance of the first eigenvalue $ev_d(m, rx)$ can be approximated by $1/(1-CF_1(m, rx))$, where $CF_1(m, rx)$ is a coherence factor obtained from channel data S(m, n, tx, rx). Temporal averaging 230, averaging over multiple transmit beams 116, 118, and/or RDT can be applied in calculating $CF_1(m, rx)$. Inversely, coherence factor can be approximated by eigenvalue dominance derived with proper averaging.

FIGS. 3A-3D relate to the portion of the ultrasonic microcalcification identification process up until metric calculation. The procedure described below is an example of live, dynamic, real-time imaging, although it can be simplified to return a single B-mode image bearing the distinguished calcifications.

Figure 3A:
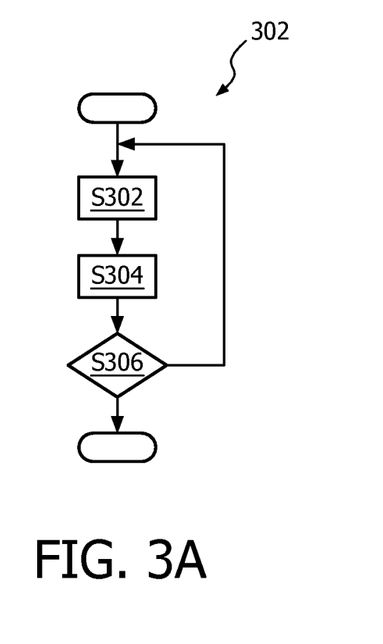
FIGS. 3A-3D, 4A-4C, and 5 are flow charts of an exemplary ultrasonic microcalcification identification process in accordance with the present invention.

In accordance with a scanning process 302, shown in FIG. 3A, transmits 116, 118 are issued (step S302). This can be done serially on transmit in a range around the center 152 of the receive beam 150 using for example RDT scanning sequences. For each transmit there can be multiple receive beams, leading to multiple transmits per receive beam. Or a single transmit 116 may be issued per receive beam 150 as is done for the estimating of $CF_0(m, rx)$, the estimate without beam averaging. In the case of a single transmit or in the case of multiple ones, for each transmit there is a receive, via the receive beam 150 (step S304) or there are multiple receives. The transmits 116 and receives 150 proceed, until scanning is complete or otherwise halted (step S306).

Figure 3B:
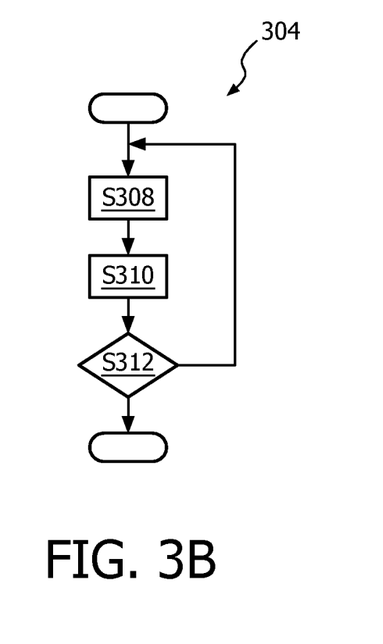

A concurrent channel data acquisition subprocess 304, shown in FIG. 3B, acquires complex channel data (step S308), and delays the data samples by channel (step S310). This occurs repeatedly, until scanning is complete or otherwise halted (step S312).

Figure 3C:
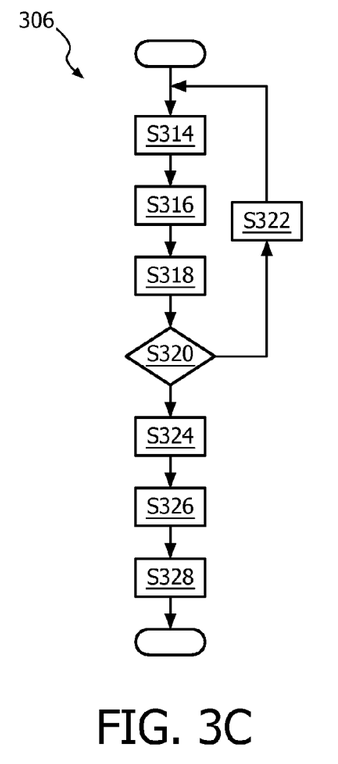

In a concurrent coherence factor estimation subprocess 306, seen in FIG. 3C, samples that vary by channel are obtained (step S314). They are coherently summed, thereby completing a beamforming procedure (step S316). The magnitude of each sample is calculated channel by channel (step S318). If there exists a next transmit 116, for beam averaging, for the current spatial point 146 being interrogated (step S320), a transmit counter is incremented (step S322), and processing returns to the sample-obtaining step S314. Otherwise, if there does not exist a next transmit 116 (step S320), the transmit counter is reset (step S324). Summation for beamforming and summation of sample magnitudes are performed over all transmits 116 for the current spatial point 146 (step S326). The coherence factor CF 204 is computed (step S328).

Figure 3D:
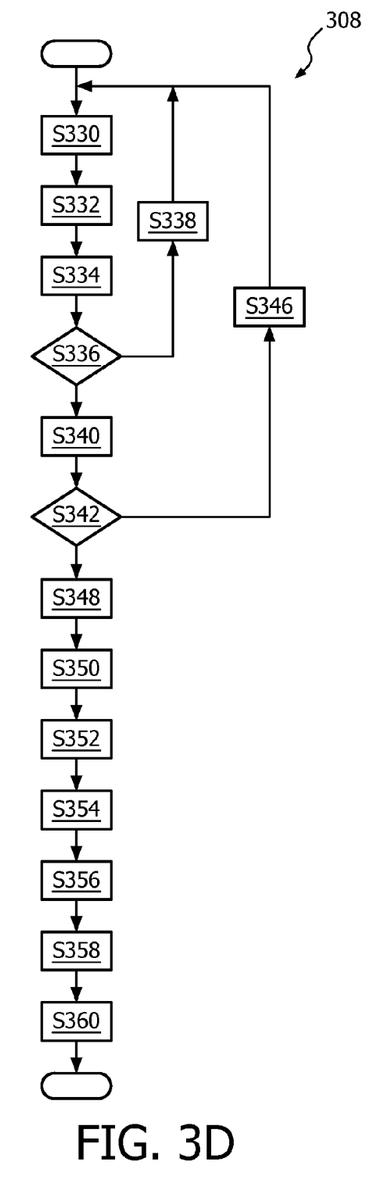

Meanwhile, in a concurrent dominance derivation subprocess 308 of FIG. 3D, samples are obtained that vary by channel (step S330). A conjugate transpose 220 of a column matrix of the samples ordered by channel is formed (step S332). A product 222 is taken of the two matrices (step S334). If a next transmit 116, for beam averaging, exists for the current spatial point 146 (step S336), the transmit counter is incremented (step S338) and processing returns to the sample acquisition step S330. Otherwise, if a next transmit 116 does not exist (step S336), the transmit counter is reset (step S340). Query is then made as to whether a next neighbor point 224 for temporal averaging exists (step S342). If a next neighbor point 224 exists (step S342), the neighbor point counter is incremented (step S346) and processing returns to the sample acquisition step S330. Otherwise, if a next neighbor point 224 does not exist (step S342), the neighbor counter is reset (step S348). The product matrix from step S334 is summed over the transmits 116 and neighbor points 224 (step S350). As seen from definition 2 in FIG. 2, a covariance matrix with beam averaging 226 is computed based on the summed products 222 (step S352). A set of eigenvalues 212 are computed for the covariance matrix 226 by methods well known in the art (step S354). The largest 218 from among the eigenvalues is found (step S356). It is compared 228 with the set (step S358). The dominance 216 is calculated (step S360).

Figure 4A:
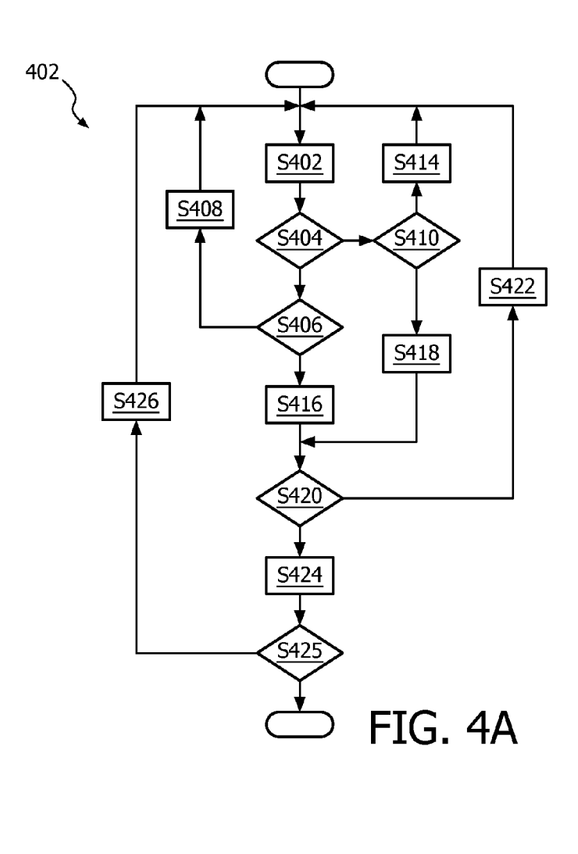

The estimation and derivation subprocesses 306, 308 are executed in the context of scanning subprocess 402 which is presented in FIG. 4A. In a first step, a metric is computed for the current spatial point 146 (step S402). Step S402 corresponds to either the estimation or derivation subprocess 306, 308. Accordingly, both the coherence factor (CF) determination module 120 and the eigenvalue dominance determination module 122 invoke the instant scanning subprocess 402. If time, rather than spatial depth, is being indexed for temporal tracking (step S404), and a next time exists for the current receive beam 150 (step S406), the time counter is incremented (step S408) and return is made to step S402. Likewise, if, instead of time, spatial depth is being indexed for temporal tracking (step S404), and a next spatial depth exists for the current receive beam 150 (step S410), the spatial depth counter is incremented (step S414) and return is made to step S402. If, on the other hand, no next time or spatial depth exists (steps S406, S410), correspondingly the time or spatial depth counter is reset (steps S416, S418). If, at this juncture, a next receive beam 150 exists in the current frame or scan (step S420), the receive beam counter is incremented (step S422). Otherwise, if no next receive beam 150 exists (step S420), the receive counter is reset (S424). If a next frame exists (step S425), processing points to the next frame (step S426) and return is made to the metric computation step S402.

Figure 4B:
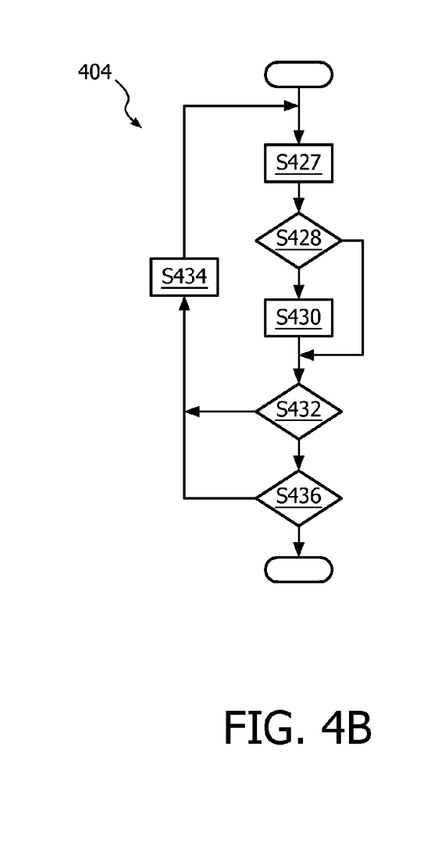

The microcalcification identification module 124 concurrently executes a first version 404 of a microcalcification mapping subprocess, shown in FIG. 4B. First, the CF 204 and the dominance 216 are combined, as by multiplication (step S427). If the product is large enough to meet a combination threshold (step S428), the respective (and current) spatial point 146 is added to the microcalcification map for the current imaging frame (step S430). A microcalcification 142 has therefore been distinguished from background 148. If there is a next point in the frame (step S432), processing points to that next point (step S434) and return is made to the start of the subprocess 404. Otherwise, if there is no next point in the current frame (step S432), but there is a next frame to process (step S436), processing points to the next point (step S434) and return is made to the start of the subprocess 404.

Figure 4C:
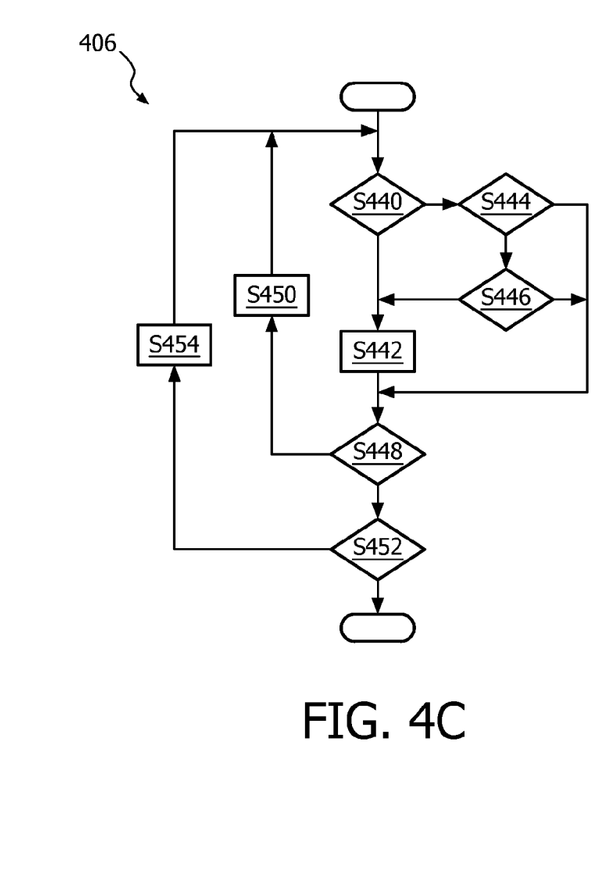

Alternatively or in addition, the microcalcification identification module 124 concurrently executes a second version 406 of a microcalcification mapping subprocess, as seen from FIG. 4C. If a first coherence threshold is met, i.e., the CF 204 is large enough to meet it (step S440), the current spatial point 146 is added to the microcalcification map for the current imaging frame (step S442). On the other hand, even if the first coherence threshold is not met (step S440), but the CF 204 is large enough to meet another, i.e., second, predetermined coherence threshold (step S444) and the dominance 216 is large enough to meet a dominance threshold (step S446), the current spatial point 146 is added to the microcalcification map (step S442). If a next point exists in the current frame (step S448), processing points to that next point (step S450) and return is made to step S440. If, on the other hand, with the first coherence threshold not being met (step S440), if either the second coherence threshold or dominance threshold is likewise not met or both are not met (steps S444, S446), and if a next point exists (step S448), processing points to that next point (step S450) and return in made to step S440. In any event, when no next point in the current frame exists (step S448), if a next frame exists (step S452), processing points to that next frame (step S454) and return is made to step S440.

Figure 5:
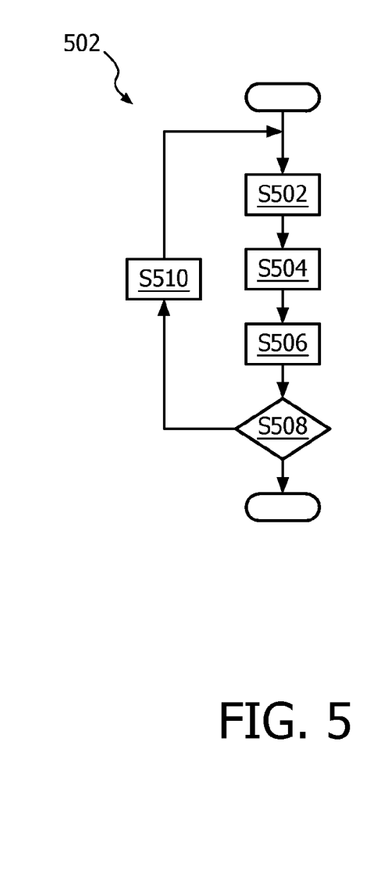

The microcalcification identification module 124 is also concurrently invoking a visual calcification discrimination subprocess 502, represented in FIG. 5. To the current frame for display, the corresponding microcalcification map is applied (step S502). All spatial points 146, e.g., voxels, in the current frame have been processed in either the first or second versions 404, 406 of the microcalcification mapping subprocess. The entries of the current microcalcification map denote microcalcifications 142 and are to be distinguished visually for presentation on-screen (step S504). This is done by highlighting, coloring or distinctive coloring, annotation with labels and/or screen pointers, etc., and is done by means of overlays, the adjustment of grey level, or any other known and suitable means. The image bearing the distinguished calcifications is displayed (step S506). If a next frame exists (step S508), processing points to that next frame (step S510), and returns to the map application step S502.

A medical ultrasound acquisition-data analysis device acquires channel data via ultrasound received on the channels, uses the acquired channel data to estimate data coherence and derive dominance of an eigenvalue of a channel covariance matrix and, based on the estimate and dominance, distinguishes microcalcifications from background. Microcalcifications may then be made distinguishable visually onscreen via highlighting, coloring, annotation, etc. The channel data operable upon by the estimating may have been subject to beamforming delays and may be summed in a beamforming procedure executed in the estimating. In the estimating and deriving, both field point-by-field point, multiple serial transmits may be used for each field point. In one embodiment results of the estimating and deriving are multiplied point-by-point and submitted to thresholding.

While the invention has been illustrated and described in detail in the drawings and foregoing description, such illustration and description are to be considered illustrative or exemplary and not restrictive; the invention is not limited to the disclosed embodiments.

For example, within the intended scope of what is proposed herein is a computer readable medium, as described below, such as an integrated circuit that embodies a computer program having instructions executable for performing the subprocesses 306, 308, 404, 406, 502 described above for microcalcification discrimination. The functions are implementable by any combination of software, hardware and firmware.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A medical ultrasound acquisition-data analysis device comprising:
    a beamformer that acquires channel data from a plurality of channels via ultrasound received on the channels;
    a coherence factor determinator that uses the acquired channel data to estimate coherence of points in the channel data; and
    an eiqenvalue determinator that derives dominance of eigenvalues of a channel covariance matrix based on the channel data; and,
    a microcalcification identifier that uses the estimated coherence and the derived dominance to distinguish microcalcifications from background; and
    a signal processor circuit that forms an image based on the channel data, wherein the signal processor circuit identifies the distinguished microcalcifications on the image.

2. The device of claim 1, comprising a display, wherein the signal processor circuit displays the distinguished microcalcifications in an ultrasound view.

3. The device of claim 2, further configured for displaying on the display, the microcalcifications in a presentation that, based on a result of the distinguishing, visually discriminates the microcalcifications from the background.

4. The device of claim 1, wherein the coherence factor determinator uses the data individually with respect to a plurality of spatial points having respectively an associated receive beam and a time or spatial depth.

5. The device of claim 4, wherein the coherence factor determinator uses the channel data to estimate the coherence separately by point with respect to the plurality of points.

6. The device of claim 4, wherein the microcalcification identifier combines the estimates of coherence and the dominance of each point to identify microcalcification.

7. The device of claim 6, wherein the combining comprises multiplying the estimates of coherence by the dominance of each point.

8. The device of claim 6, wherein the microcalcification classifier uses thresholding to distinguish the microcalcifications from the background.

9. The device of claim 1, wherein the coherence factor determinator estimates coherence factors by summing, over multiple transmit beams, a function of the data with respect to a given receive beam and a given time or spatial depth.

10. The device of claim 9, wherein the estimating comprises summing the function over the channels.

11. The device of claim 1, wherein the matrix is characterized by a plurality of eigenvalues, and the dominance comprises a metric representing a comparison between each eigenvalue and the plurality of eigenvalues.

12. The device of claim 1, wherein the channel data comprises complex radiofrequency channel data to which beamforming delays have been applied, and the eigenvalue determinator derives the dominance by taking a conjugate transpose of a matrix of the channel data, entries of the conjugate transpose varying by channel.

13. The device of claim 12, wherein the eigenvalue determinator derives the dominance by: forming a product matrix, the forming comprising multiplying the matrix of the channel data by the conjugate transpose; and averaging the product matrix over a range of spatial depth or time to derive the dominance corresponding to a given spatial point.

14. The device of claim 12, wherein the eigenvalue determinator derives the dominance by: forming a product matrix, the forming comprising multiplying the matrix of the channel data by the conjugate transpose; and averaging the product matrix over multiple transmits.

15. The device of claim 12, wherein the complex radiofrequency channel data is created using an algorithm that recreates focused transmit beams retrospectively.

16. The device of claim 1, wherein the microcalcification identifier decides whether a microcalcification resides at a given spatial point based on application of a coherence threshold to the estimated coherence.

17. The device of claim 16, wherein, if the decision is other than that a microcalcification resides at the given spatial point, determining whether estimated coherence and the derived dominance respectively meet another coherence threshold and a dominance threshold to decide whether a microcalcification resides at the spatial point.

18. The device of claim 1, wherein the background comprises body tissue in which the microcalcifications reside.

19. The device of claim 1, wherein the beamformer acquires the channel data from an ultrasound probe having a spatial resolution, and wherein the microparticles are smaller than the spatial resolution of the ultrasound probe.

20. A method comprising:
receiving, at a beamformer, channel data from a plurality of channels via ultrasound received on the channels;
estimating, by a coherence factor determinator, a coherence factor for each point in the channel data;
determining, by an eigenvalue determinator, eigenvalues of a covariance matrix based on the channel data, and a dominance of each eigenvalue corresponding to each point in the channel data;
identifying, by a microcalcification identifier, microcalcifications based on the coherence factor and the dominance of each point in the channel data; and
identifying, by a signal processor, the microcalcifications on an image that is formed based on the channel data.

21. The method of claim 20, further comprising multiplying, at the microcalcification identifier, the coherence factor and the dominance of each point to identify whether the point comprises a microcalcification.

22. The method of claim 20, further comprising estimating, at the coherence factor determinator, each coherence factor by summing, over multiple transmit beams, a function of the data that is based on a given receive beam and a given time or spatial depth.

23. The method of claim 20, further comprising deriving, at the eigenvalue determinator, the dominance by: forming a product matrix by multiplying the matrix of the channel data by a conjugate transpose of the matrix; and averaging the product matrix over a range of spatial depth or time to derive the dominance corresponding to a given spatial point.

24. The method of claim 20, further comprising determining, at the eigenvalue determinator, the dominance by taking a conjugate transpose of a matrix of the channel data, entries of the conjugate transpose varying by channel and the channel data comprising complex radiofrequency channel data to which beamforming delays have been applied.

* * * * *